(12) United States Patent
Bickford et al.

(10) Patent No.: US 10,564,200 B2
(45) Date of Patent: *Feb. 18, 2020

(54) ELECTRIC FIELD DETECTOR SYSTEM

(71) Applicant: THE CHARLES STARK DRAPER LABORATORY, INC., Cambridge, MA (US)

(72) Inventors: James A. Bickford, Winchester, MA (US); Marc S. Weinberg, Needham, MA (US); John Shattler Fullford, Newbury, MA (US); Ronald Steven McNabb, Jr., Charlestown, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 372 days.

This patent is subject to a terminal disclaimer.

(21) Appl. No.: 15/286,163

(22) Filed: Oct. 5, 2016

(65) Prior Publication Data
US 2017/0097382 A1 Apr. 6, 2017

Related U.S. Application Data

(60) Provisional application No. 62/370,454, filed on Aug. 3, 2016, provisional application No. 62/237,841, filed on Oct. 6, 2015.

(51) Int. Cl.
| | |
|---|---|
| *G01R 29/08* | (2006.01) |
| *A61B 5/0478* | (2006.01) |
| *A61B 5/04* | (2006.01) |

(52) U.S. Cl.
CPC ............ *G01R 29/0878* (2013.01); *A61B 5/04* (2013.01); *A61B 5/0478* (2013.01);
(Continued)

(58) Field of Classification Search
CPC .. G01R 29/0878; G01R 29/0814; A61B 5/04; A61B 5/0478; A61B 2562/0219; A61B 2560/0252; A61B 2562/0209
See application file for complete search history.

(56) References Cited

U.S. PATENT DOCUMENTS

| | | |
|---|---|---|
| 4,380,735 A | 4/1983 | Bell |
| 4,670,092 A | 6/1987 | Motamedi |

(Continued)

FOREIGN PATENT DOCUMENTS

| | | |
|---|---|---|
| CN | 102879655 A | 1/2013 |
| CN | 103390478 A | 11/2013 |

(Continued)

OTHER PUBLICATIONS

Williams et al., "Vacuum Steered-Electron Electric-Field Sensor", Journal of Microelectromechanical Systems, pp. 1-10, Jan. 15, 2013.

(Continued)

*Primary Examiner* — Huy Q Phan
*Assistant Examiner* — Zannatul Ferdous
(74) *Attorney, Agent, or Firm* — Lando & Anastasi, LLP

(57) ABSTRACT

Aspects and embodiments are generally directed to electric field detector systems and methods. In one example, an electric field detector system includes a proof-mass including a source of concentrated charge, a plurality of supports, each individual support of the plurality supports being coupled to the proof-mass, a plurality of sensors, each individual sensor of the plurality of sensors positioned to measure a resonant frequency of a corresponding support of the plurality of supports, and a controller coupled to each individual sensor of the plurality of sensors, the controller configured to measure a characteristic of an electric field (Continued)

imparted on the proof-mass based on at least a first resonant frequency of the measured resonant frequencies.

20 Claims, 11 Drawing Sheets

(52) U.S. Cl.
CPC .. *G01R 29/0814* (2013.01); *A61B 2560/0252* (2013.01); *A61B 2562/0219* (2013.01)

(56) References Cited

U.S. PATENT DOCUMENTS

| | | | |
|---|---|---|---|
| 5,908,986 A | 6/1999 | Mitamura | |
| 5,945,898 A | 8/1999 | Judy et al. | |
| 6,250,156 B1 | 6/2001 | Seshia et al. | |
| 6,429,652 B1* | 8/2002 | Allen | G01C 17/28 324/259 |
| 6,487,864 B1 | 12/2002 | Platt et al. | |
| 6,670,809 B1 | 12/2003 | Edelstein et al. | |
| 6,874,363 B1 | 4/2005 | Foote et al. | |
| 7,185,541 B1 | 3/2007 | Edelstein | |
| 7,231,094 B2 | 6/2007 | Bickford et al. | |
| 7,394,245 B2 | 7/2008 | Brunson et al. | |
| 7,642,692 B1 | 1/2010 | Pulskamp | |
| 7,773,228 B1 | 8/2010 | Hollingsworth et al. | |
| 7,972,888 B1 | 7/2011 | Li et al. | |
| 8,205,497 B1* | 6/2012 | Okandan | G01C 19/5712 73/514.26 |
| 8,674,689 B1 | 3/2014 | Nielson et al. | |
| 8,701,490 B2* | 4/2014 | Jiang | G01P 15/125 73/514.32 |
| 9,182,454 B1 | 11/2015 | Williams et al. | |
| 2002/0162947 A1 | 11/2002 | Weitekamp et al. | |
| 2003/0140699 A1 | 7/2003 | Pike et al. | |
| 2003/0200807 A1 | 10/2003 | Hulsing | |
| 2004/0187578 A1* | 9/2004 | Malametz | B81B 3/0072 73/514.36 |
| 2005/0234329 A1 | 10/2005 | Kraus et al. | |
| 2006/0032306 A1 | 2/2006 | Robert | |
| 2007/0096729 A1 | 5/2007 | Brunson et al. | |
| 2010/0099942 A1 | 4/2010 | Portelli | |
| 2011/0048133 A1 | 3/2011 | Lin et al. | |
| 2011/0054345 A1 | 3/2011 | Nagatani | |
| 2011/0056294 A1* | 3/2011 | Simoni | G01P 15/097 73/514.29 |
| 2011/0062820 A1* | 3/2011 | Aoyagi | H02N 1/08 310/300 |
| 2014/0023999 A1 | 1/2014 | Greder | |
| 2014/0125325 A1* | 5/2014 | Ocak | G01R 33/0286 324/207.13 |
| 2014/0182377 A1 | 7/2014 | Lin et al. | |
| 2014/0308757 A1 | 10/2014 | Ju | |
| 2014/0358016 A1 | 12/2014 | Shapira et al. | |
| 2015/0226762 A1* | 8/2015 | Seshia | G01P 1/006 73/495 |
| 2016/0023002 A1* | 1/2016 | Schulhauser | G01R 33/0052 600/411 |
| 2016/0081577 A1 | 3/2016 | Sridhar et al. | |
| 2016/0116499 A1 | 4/2016 | Thompson | |
| 2016/0120432 A1 | 5/2016 | Sridhar et al. | |
| 2016/0341762 A1* | 11/2016 | Waters | G01C 19/04 |
| 2016/0349283 A1* | 12/2016 | Bramhavar | G01P 15/097 |
| 2017/0276697 A1* | 9/2017 | Campsie | G01P 15/13 |
| 2017/0281086 A1 | 10/2017 | Donaldson | |

FOREIGN PATENT DOCUMENTS

| | | |
|---|---|---|
| CN | 103342562 B | 2/2015 |
| CN | 104459351 A | 3/2015 |
| CN | 106093605 A | 11/2016 |
| DE | 102014204721 A1 | 9/2015 |
| EP | 0702981 A1 | 3/1996 |
| EP | 2199741 A2 | 6/2010 |
| EP | 2466257 A1 * | 6/2012 ............ G01C 19/56 |
| JP | 2011136158 A | 7/2011 |
| WO | 02084315 A1 | 10/2002 |
| WO | 2012071545 A1 | 5/2012 |
| WO | 2014025353 A1 | 2/2014 |
| WO | 2014205356 A2 | 12/2014 |

OTHER PUBLICATIONS

Ando et al., "E-Field Ferroelectric Sensor: Modeling and Simulation", IEEE Instrumentation & Measurement Magazine, pp. 31-37, 2009.

Bogue, R., "Plessey launches range of unique electric field sensors", Sensor Review, vol. 32, No. 3, pp. 194-198, 2012.

Chen et al., "Micromachined ac/dc electric field sensor with modulated sensitivity", Sensors and Actuators, No. 245, pp. 76-84, Apr. 26, 2016.

Huang et al., "A novel high-sensitivity electrostatic biased electric field sensor", Journal of Micromechanics and Microengineering, vol. 25, pp. 1-9, Aug. 17, 2015.

Miles et al., "Report on Non-Contact DC Electric Field Sensors", Jun. 23, 2009.

Datskos et al., "Using Micro-Electro-Mechanical Systems (MEMS) as Small Antennas", IEEE, 2012.

Toney et al., "Detection of Energized Structures with an Electro-Optic Electric Field Sensor", IEEE, pp. 1364-1369, May 2014.

Petrov et al., "Electric Field Encephalography as a Tool for Functional Brain Research: A Modeling Study", PLOS One, vol. 8, No. 7, Jul. 3, 2013.

International Search Report and Written Opinion for application No. PCT/US2016/055584 dated Jul. 27, 2017.

Angelakis et al., "EEG Neurofeedback: A Brief Overview and an Example of Peak Alpha Frequency Training for Cognitive Enhancement in the Elderly", The Clinical Neuropsychologist, vol. 21, pp. 110-129, Feb. 16, 2007.

Ashrafulla, S., "EEG and MEG: functional brain imaging with high temporal resolution", Jun. 2013, <URL: https://hgp.usc.edu/files/2013/06/Syed_EEG_MEG.pdf>.

Basar et al., "A review of brain oscillations in cognitive disorders and the role of neurotransmitters", Brain Research, vol. 1235, pp. 172-193, Jul. 2, 2008.

Bernstein et al., "Low-Noise MEMS Vibration Sensor for Geophysical Applications", Journal of Microelectromechanical Systems, vol. 8, No. 4, pp. 433-438, Dec. 1999.

Choi, K., "Electroencephalography (EEG) based neurofeedback training for brain-computer interface (BCI)", pp. 1-26, Sep. 2013.

Dilella et al., "A Micromachined Magnetic-Field Sensor Based on an Electron Tunneling Displacement Transducer", Sensors and Actuators, vol. 86, pp. 8-20, 2000.

Dong et al., "Push-Pull Mode Magnetostrictive/Piezoelectric Laminate Composite with an Enhanced Magnetoelectric Voltage Coefficient", Applied Physics Letters, vol. 87, p. 62502, 2005.

Gabrielson, T.B., "Mechanical-Thermal Noise in Micromachined Acoustic and Vibration Sensors", IEEE Transactions On Electron Devices, vol. 40, No. 5, pp. 903-909, May 1993.

Grummett et al., "Measurement of neural signals from inexpensive, wireless and dry EEG systems", Physiological Measurement, vol. 36, pp. 1469-1484, 2015.

Heintzelman et al., "Characterization and Analysis of Electric-field Sensors", IEEE, Dec. 17, 2015.

Kingsley et al., "Photrodes for physiological sensing", SPIE 5317, Optical Fibers and Sensors for Medical Applications IV, Jun. 2004.

Kyynaerainen et al., "A 3D Micromechanical Compass", Sensors and Actuators A, vol. 142, pp. 561-568, 2008.

Latorre et al., "Micromachined CMOS Magnetic Field Sensor with Ferromagnetic Actuation", Proceedings of SPIE, vol. 4019, 2000.

Niv, S., "Clinical efficacy and potential mechanisms of neurofeedback", Personality and Individual Differences, vol. 54, pp. 676-686, Jan. 24, 2013.

Othmer, S., "Neuromodulation technologies: An attempt at classification", Introduction to Quantitative EEG and Neurofeedback: Advanced Theory and Applications, second edition, pp. 1-27, 2009.

(56) References Cited

OTHER PUBLICATIONS

Prance, H., "Sensor Developments for Electrophysiological Monitoring in Healthcare", Applied Biomedical Engineering, pp. 265-286, Aug. 2011.
Schalk et al., "Brain Sensors and Signals", A Practical Guide to Brain-Computer Interfacing with General-Purpose Software for Brain-Computer Interface Research, Data Acquisition, Stimulus Presentation, and Brain Monitoring, pp. 9-35, 2010.
Stikic et al., "Modeling temporal sequences of cognitive state changes based on a combination of EEG-engagement, EEG-workload, and heart rate metrics", Frontiers in Neuroscience, vol. 8, article 342, pp. 1-14, Nov. 2014.
Tatarchuk et al., "A MEMS DC Current Sensor Utilizing Neodymium Rare Earth Magnets", Advancing Microelectronics, pp. 6-10, Jan. 2015.
Vasquez, D., and J. Judy, "Optically-Interrogated Zero-Power MEMS Magnetometer", Journal of Microelectromechanical Systems, vol. 16, No. 2, pp. 336-343, Apr. 2007.
Wickenden et al., "Polysilicon Xylophone Bar Magnetometers", SPIE, vol. 3876, pp. 267-273, Sep. 1999.
Yang et al., "Ferromagnetic Micromechanical Magnetometer", Sensors and Actuators A, vol. 97-98, pp. 88-97, 2002.
Zhao et al., "Fabrication and Characterization of All-Thin-Film Magnetoelectric Sensors", Applied Physics Letters, vol. 94, p. 243507, 2009.
U.S. Appl. No. 14/919,527, filed Oct. 21, 2015, Bickford et al.
Budzynski et al., "Introduction to Quantitative EEG and Neurofeedback: Advanced Theory and Applications," 2nd ed., Elsevier (2009), chapters 1, 6, 8 and 16.
Denison et al., "A Self-Resonant MEMS-Based Electrometer", IEEE Instrumentation and Measurement Technology Conference Proceedings, May 2007, pp. 1-5.
Bickford, J. "Monitoring Brain Activity (E-Field Sensor)", Draper, accessed Oct. 31, 2016.
Kelly et al., "Progress Toward Forecasting of Space Weather Effects on UHF Satcom after Operation Anaconda", Space Weather, Sep. 12, 2014, doi: 10.1002/2014SW001081.
Chen et al. "MEM Electric Field Sensor using Force Deflection with Capacitance Interrogation", Power & Energy Society General Meeting. IEEE (2013).
Kuriyama et al. "Electrostatic Field Distribution Measurement Using Silicon Micro-mirror Array", IEEE International Symposium on Electromagnetic Compatibility (2012), pp. 351-356.
Goel, M. "Electret sensors, filters and MEMS devices: New challenges in materials research", Current Science (2003) vol. 85, No. 4, pp. 443-453.

\* cited by examiner

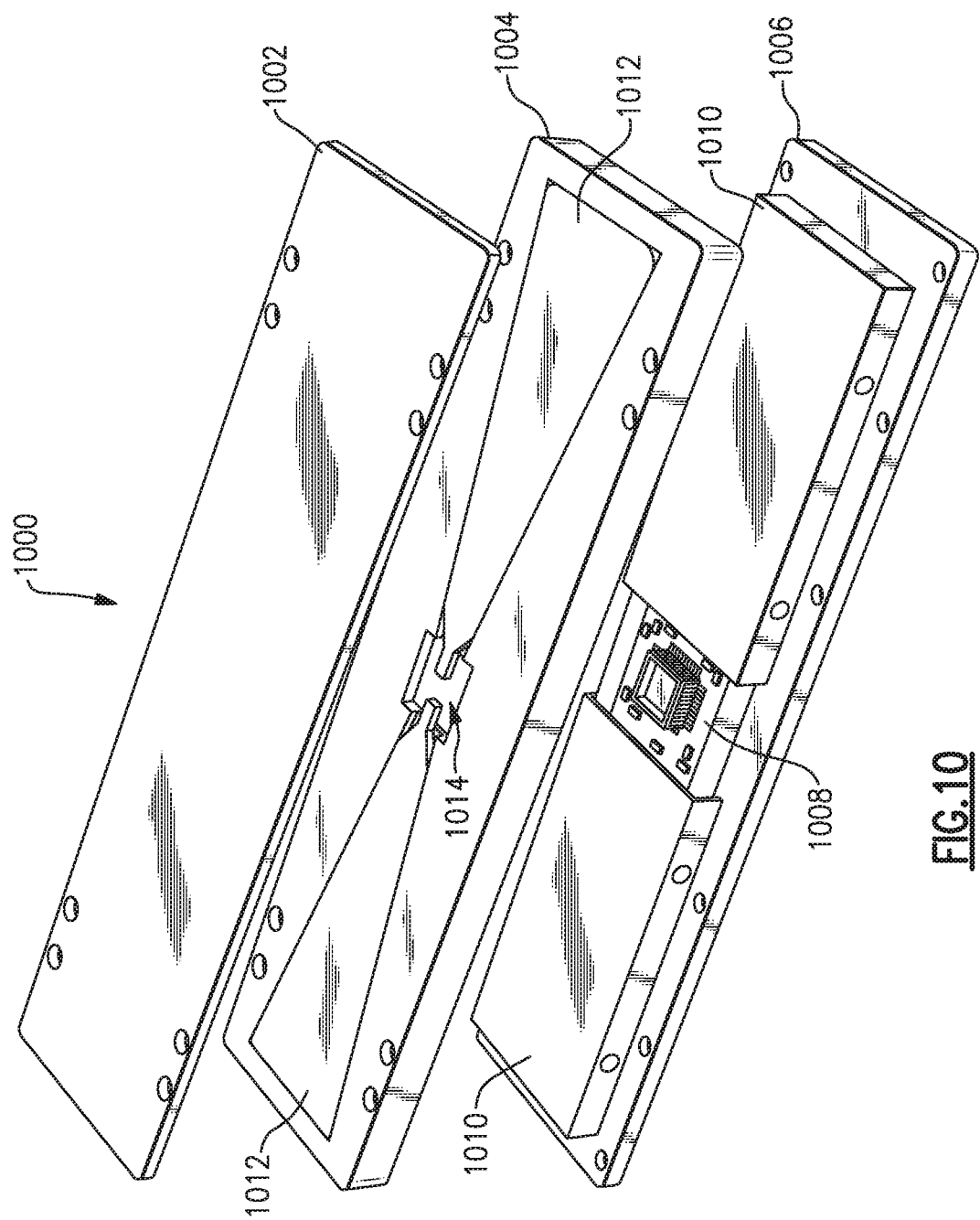

ELECTRIC FIELD DETECTOR SYSTEM

CROSS-REFERENCE TO RELATED APPLICATIONS

This application claims priority under 35 U.S.C. § 119 (e) to U.S. Provisional Application Ser. No. 62/237,841, titled "ELECTRIC FIELD DETECTOR SYSTEM," filed on Oct. 6, 2015, which is hereby incorporated herein by reference in its entirety. This application also claims priority under 35 U.S.C. § 119 (e) to U.S. Provisional Application Ser. No. 62/370,454, titled "ELECTRIC FIELD DETECTOR SYSTEM," filed on Aug. 3, 2016, which is hereby incorporated herein by reference in its entirety.

BACKGROUND

Equipment that is electrically operated, or that incorporates moving structures containing electrically conductive materials or charged dielectrics, will generate static and time-varying electromagnetic fields during operation. These fields may be faint even in close proximity to the source, and will attenuate as the distance from the source is increased. Nevertheless, detectable components of these signals may exist at great distances from the source. Often great care is taken to design equipment, such as military equipment, to minimize the likelihood that unintended electromagnetic emissions will reveal the location of the equipment. Despite the care taken to reduce such emissions, low level electromagnetic signals may still exist at great distances and can be measured. Weak electromagnetic signals may also be utilized in numerous other applications, such as in communication systems, natural resource exploration, scientific research, meteorological monitoring, localization, and navigation.

Similarly, various bio-physical signals are generated by the human body. For example, ionic currents within neurons of the brain will generate voltage fluctuations and magnetic fields during synaptic transmission. Although these signals may be weak, they can be measured and used in various diagnostic applications. Conventionally, numerous highly sensitive magnetometers are employed during magnetocephalography to detect magnetic fields, and numerous electrodes are employed during electroencephalography to detect electrical activity.

SUMMARY

Aspects and embodiments are directed to systems and methods for exploiting the electric component of electromagnetic signals. There is a need for improved detectors which enhance the ability to measure small fields emitted by equipment or natural processes. Systems may include one or more electric field detectors capable of detecting an electric field generated by equipment that has been designed to reduce unintended electromagnetic emissions, or that naturally generates very small or attenuated electric and magnetic field signals. In further aspects and embodiments, one or more electric field detector described herein permits the detection and analysis of weak bio-physical signals, such as electric fields of a brain or heart of a patient or user. Such aspects and embodiments allow non-invasive and non-contact observation of the user's state or condition.

The performance of an electric field detector is generally limited by the noise that contributes to its measurement. Operation of the detector and environmental conditions both contribute to the noise, which affects the resolution of the system. With shielding or removal of background noise, conventional detectors still experience severe difficulty measuring weak electric field signals due to the sensor noise. Accordingly, there is a need for an improved electric field detector capable of observing weak electric fields, and certain aspects and embodiments are directed to meeting this need.

According to certain aspects, an improved electric field detector system is provided. In one example, the system includes a proof-mass including a source of concentrated charge, a plurality of supports, each individual support of the plurality supports being coupled to the proof-mass, a plurality of sensors, each individual sensor of the plurality of sensors positioned to measure a resonant frequency of a corresponding support of the plurality of supports, and a controller coupled to each individual sensor of the plurality of sensors, the controller configured to measure a characteristic of an electric field imparted on the proof-mass based on at least a first resonant frequency of the measured resonant frequencies.

In certain examples, the controller is further configured to determine a linear force imparted on the proof-mass, in a first direction, based on at least the first resonant frequency of the measured resonant frequencies. According to one example, the controller is further configured to determine a temperature based on a common mode signal generated from a comparison of each of the measured resonant frequencies. In one example, the characteristic of the electric field includes an electric field strength, and wherein in measuring the characteristic of the electric field the controller is configured to compare at least the first resonant frequency to a first frequency reference to measure a torque on the proof-mass. According to some examples, the resonant frequency of each support includes a natural frequency.

According to one example, the plurality of supports includes a first support coupled to a first side of the proof-mass and having the first resonant frequency, a second support coupled to a second side of the proof-mass and having a second resonant frequency, a third support coupled to the first side of the proof-mass and having a third resonant frequency, and a fourth support coupled to the second side of the proof-mass and having a fourth resonant frequency. In some examples, the controller is further configured to determine a first linear force imparted on the proof-mass, in a first direction, and a second linear force imparted on the proof-mass, in a second direction, based on the first resonant frequency, the second resonant frequency, the third resonant frequency, and the fourth resonant frequency, and determine a temperature based on a common mode signal generated from a comparison of each of the first resonant frequency, the second resonant frequency, the third resonant frequency, and the fourth resonant frequency.

According to one example, the source of concentrated charge includes a polarized ferro-electric material including Lithium Niobate. In some examples, the source of concentrated charge includes an electret. In one example, the electret includes a plurality of stacked electrets.

According to some examples, each sensor of the plurality of sensors includes a comb drive including a first electrode configured to apply a voltage to a comb positioned on the corresponding support, and a second electrode configured to measure a change in a capacitance between the first electrode and the second electrode, wherein the controller is further configured to infer the resonant frequency of the corresponding support based at least in part on the change in the capacitance.

In one example, the system may further include a field concentrator located adjacent a side of the proof-mass, the field concentrator positioned so as to focus the electric field on the proof-mass. According to certain examples, the system may further include a housing, the system is disposed within the housing. In one example, the housing includes at least one attachment to secure the system to a mobile platform. According to another example, the housing includes at least one attachment to secure the system to a stationary platform.

According to certain examples, the system further includes a plurality of geometric isolation structures interposed between the proof-mass and each of the plurality of supports, each geometric isolation structure being positioned to isolate a respective support from a differential thermal strain between the proof-mass and the respective support. In one example, the system further includes an internal isolation structure extending through the proof-mass and configured to suspend the proof-mass relative to a system substrate, the internal isolation structure being positioned to isolate the plurality of supports from a differential thermal strain between the proof-mass and the plurality of supports.

Certain aspects are directed to an electric field transduction method. In one example, the method includes generating an electric dipole at a proof-mass coupled to a plurality of supports, receiving an electric field at the proof-mass, measuring a resonant frequency of each individual support of the plurality of supports, and determining a characteristic of the electric field based on at least one resonant frequency of the measured resonant frequencies.

According to some examples, determining the characteristic of the electric field further includes comparing the at least one resonant frequency to a frequency reference and determining a torque imparted on the proof-mass. In one example, determining the characteristic of the electric field includes determining the strength and variability of the electric field. According to some examples, the transduction method may further include determining a linear force imparted on the proof-mass, in a first direction, based on the at least one resonant frequency of the measured resonant frequencies. In another example, the transduction method may further include determining a temperature based on a common mode signal generated from a comparison of each of the measured resonant frequencies. In some examples, the method may further include determining a force of acceleration imparted on the proof-mass based on the at least one resonant frequency of the measured resonant frequencies of the individual supports. In certain examples, the method may further include optically sensing a displacement of the proof-mass responsive to receiving the electric field.

According to one example, the measured resonant frequency of each individual support of the plurality of supports includes a natural frequency. In one example, the method further includes sensing a variation in a capacitance between the proof-mass and a reference structure responsive to receiving the electric field.

According to one example, the plurality of supports includes a first support having a first resonant frequency, a second support having a second resonant frequency, a third support having a third resonant frequency, and a fourth support having a fourth resonant frequency, and wherein the method may further include determining a first linear force imparted on the proof-mass, in a first direction, based on the first resonant frequency, the second resonant frequency, the third resonant frequency, and the fourth resonant frequency, determining a second linear force imparted on the proof-mass, in a second direction, based on the first resonant frequency, the second resonant frequency, the third resonant frequency, and the fourth resonant frequency, and determining a temperature based on a common mode signal generated from a comparison of each of the first resonant frequency, the second resonant frequency, the third resonant frequency, and the fourth resonant frequency.

According to one aspect, a transduction method may include generating an electric dipole at a proof-mass coupled to a plurality of supports, receiving a bio-physical signal at the proof-mass, measuring a resonant frequency of each individual support of the plurality of supports, and determining a characteristic of the bio-physical signal based on at least one resonant frequency of the measured resonant frequencies. In one example, the bio-physical signal includes an electric field of a body of a patient. In certain examples, the electric field of the body of the patient includes an electric field of a brain, heart, nerve, or muscle, of the patient.

According to one aspect, a transduction method may include generating a source of concentrated charge on a structure, and imparting a torque on the structure responsive to receiving a field.

In one example, the structure includes a proof-mass coupled to a plurality of supports, and the method may further include measuring a resonant frequency of at least one support of the plurality of supports to determine the torque imparted on the proof-mass. In certain examples, the field includes an electric field, and the method may further include determining the strength and variability of the electric field. In one example, the method may further include determining an ambient temperature based on a common mode signal generated from a comparison of measured resonant frequencies of each individual support of the plurality of supports. According to one example, the method may further include determining a linear force imparted on the proof-mass in a first direction based on at least one resonant frequency of at least one of the plurality of supports. In some examples, the method may further include determining isolating the plurality of support from a differential thermal strain between the proof-mass and the plurality of supports. In certain examples, the method further includes measuring a displacement of the structure by measuring a change in capacitance between the structure and a reference structure. According to one example, the method may further include measuring displacement of the structure to infer the torque imparted on the proof-mass.

According to an aspect, provided is a transduction method. In one example, the method includes generating an electric dipole at a proof-mass coupled to a plurality of supports, receiving an electric field at the proof-mass, optically sensing a displacement of the proof-mass responsive to receiving the electric field, and determining a characteristic of the electric field based on at least on the displacement of the proof-mass.

According to another aspect, provided is another transduction method. In one example, the method includes generating an electric dipole at a proof-mass coupled to a plurality of supports, receiving an electric field at the proof-mass, sensing a variation in a capacitance between the proof-mass and a reference structure responsive to receiving the electric field, and determining a characteristic of the electric field based on at least the variation in the capacitance between the proof-mass and the reference structure.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Any embodiment disclosed herein may be combined with any other embodiment in any manner consistent with at least one of the objectives, aims, and needs disclosed herein, and references to "an embodiment," "some embodiments," "an alternate embodiment," "various embodiments," "one embodiment" or the like are not necessarily mutually exclusive and are intended to indicate that a particular feature, structure, or characteristic described in connection with the embodiment may be included in at least one embodiment. The appearances of such terms herein are not necessarily all referring to the same embodiment. Various aspects, embodiments, and implementations discussed herein may include means for performing any of the recited features or functions.

BRIEF DESCRIPTION OF THE DRAWINGS

Various aspects of at least one embodiment are discussed below with reference to the accompanying figures, which are not intended to be drawn to scale. The figures are included to provide illustration and a further understanding of the various aspects and embodiments, and are incorporated in and constitute a part of this specification, but are not intended as a definition of the limits of the disclosure. In the figures, each identical or nearly identical component that is illustrated in various figures is represented by a like numeral. For purposes of clarity, not every component may be labeled in every figure. In the figures:

FIG. 10 is diagram of an example of an electric field detector system packaged within a housing, according to aspects of the present disclosure.

DETAILED DESCRIPTION

Figure 1:
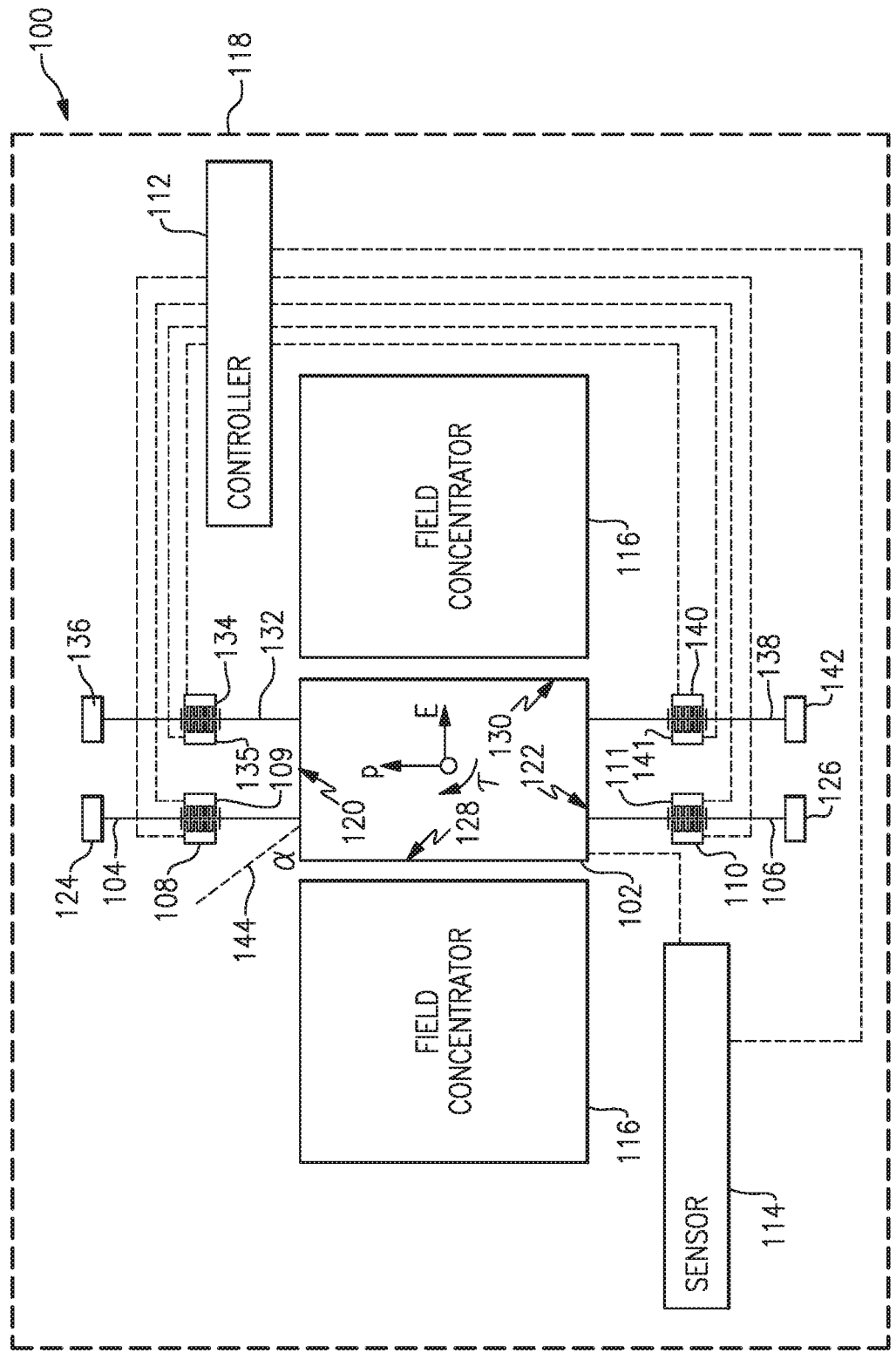
FIG. 1 is a block diagram of one example of an electric field detector system according to aspects of the present disclosure.

Aspects and embodiments are generally directed to systems and methods for exploiting the electric component of electromagnetic signals. Systems may include one or more electric field detectors capable of detecting an electric field generated by equipment or natural processes that generate electromagnetic fields. Systems may also include one or more electric field detectors capable of detecting bio-physical signals generated by the body of a patient or user, such as the electric field of his or her brain, heart, nerves or muscles.

Current electric field detectors include high noise sensors that inhibit the observation of weak electric field signals at low frequencies. While other solutions to detecting weak electric field components have been proposed, these solutions are large in size and physically restrictive.

For example, large detectors are not practical in most military or mobile applications. Furthermore, large detectors make accurate measurement of gradients in potential of a patient's scalp challenging. Typically, a dense measurement of the potential distribution is necessary for accurate measurements. For instance, this often requires EEG electrodes placed on the scalp of the patient separated by short distances. The large number of sensors required makes calculation imprecise, and often impractical in situations where electrical contact is poor (e.g., the patient has very thick hair) or inconsistent due to movement, sweating, or other factors. Accordingly, certain embodiments are directed to providing a weak electric field and/or weak bio-physical signal detector that is substantially resistant to noise, while remaining compact enough for mobile and medical applications. Accordingly, certain aspects and embodiments provide improved electric field detection systems and methods, as discussed further below.

In certain examples, systems described herein are enabled by the use of one or more sources of concentrated charge (e.g., concentrated electrical charge) coupled to a proof mass which can be measured to infer the characteristics of an electric field. The source of concentrated charge generates an electric dipole, which produces a torque when exposed to an electric field. The torque imparted on the proof-mass can be determined (e.g., directly or indirectly measured) to infer the electric field characteristics, for example, an electric field strength or variability. In one embodiment, the proof-mass is coupled to one or more mechanical supports each having a resonant frequency which can be measured to determine the torque and strength of the electric field. In various embodiments, the system further measures acceleration (e.g., linear acceleration or rotational acceleration) and temperature in addition to, or simultaneously with, the strength or variability of an electric field.

It is to be appreciated that examples and/or embodiments of the methods and systems discussed herein are not limited in application to the details of construction and the arrangement of components set forth in the following description or illustrated in the accompanying drawings. The methods and systems are capable of implementation in other embodiments and of being practiced or of being carried out in various ways. Examples of specific implementations are provided herein for illustrative purposes only and are not intended to be limiting. In particular, acts, elements and features discussed in connection with any one or more examples and embodiments are not intended to be excluded from a similar role in any other example or embodiment. Also, the phraseology and terminology used herein is for the purpose of description and should not be regarded as limiting. The use herein of "including," "comprising," "having," "containing," "involving," and variations thereof is meant to encompass the items listed thereafter and equivalents thereof as well as additional items. References to "or"

may be construed as inclusive so that any terms described using "or" may indicate any of a single, more than one, and all of the described terms. Any references to front and back, left and right, top and bottom, upper and lower, and vertical and horizontal are intended for convenience of description, not to limit the present systems and methods or their components to any one positional or spatial orientation.

The accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

FIG. 1 illustrates a block diagram of one example of an electric field detector system 100 according to various aspects and embodiments. The system 100 is shown as including a proof mass 102 including a source of concentrated charge, a plurality of supports (e.g., first support 104, second support 106, third support 132, and fourth support 138), a plurality of sensors each including a first electrode and a second electrode (i.e., a first sensor including first electrode 108 and second electrode 109, a second sensor including first electrode 110 and second electrode 111, a third sensor including first electrode 134 and second electrode 135, and a fourth sensor including first electrode 140 and second electrode 141) a controller 112, a displacement sensor 114, field concentrators 116, and a housing 118. While shown as including four supports, in further embodiments the system 100 may include any number of supports and electrode configurations. In particular, while each of the first support 104, second support 106, third support 132, and fourth support 138 are illustrated as a single beam in FIG. 1, in various other embodiments each support 104, 106, 132, 138 may be split into a double-beam fork to further reduce damping losses. In FIG. 1 the proof-mass 102 is shown as being formed from the source of concentrated charge; however, in other implementations the proof-mass 102 may be coupled (e.g., adhered or connected) to the source of concentrated charge.

As shown in one embodiment, the first support 104 is coupled between a first side 120 of the proof-mass 102 and a first mechanical ground 124. The first support 104 may include a first comb interposed between the proof-mass 102 and the mechanical ground 124. In such an embodiment, the first comb of the first support 104 may be positioned between and in electrical communication with the first electrode 108 and second electrode 109 of the first sensor. Similarly, the second support 106 is coupled between a second side 122 of the proof-mass 102 and a second mechanical ground 126. The second support 106 may include a second comb interposed between the proof-mass 102 and the second mechanical ground 126. In such an embodiment, the second comb of the second support 106 may be positioned between and in electrical communication with the first electrode 110 and the second electrode 111 of the second sensor. The third support 132 is coupled between the first side 120 of the proof-mass 102 and a third mechanical ground 136. The third support 132 may include a third comb interposed between the proof-mass 102 and the third mechanical ground 136. In such an embodiment, the third comb of the third support 132 may be positioned between and in electrical communication with the first electrode 134 and second electrode 135 of the third sensor. Similarly, the fourth support 138 is coupled between the second side 122 of the proof-mass 102 and a fourth mechanical ground 142. The fourth support 138 may include a fourth comb interposed between the proof-mass 102 and the fourth mechanical ground 142. In such an embodiment, the fourth comb of the fourth support 138 may be positioned between and in electrical communication with the first electrode 140 and the second electrode 141 of the fourth sensor. The second side 122 of the proof-mass 102 is shown substantially opposite to the first side 120 of the proof-mass 102. Each mechanical ground may be further coupled to, or formed on, a shared substrate.

Figure 2:
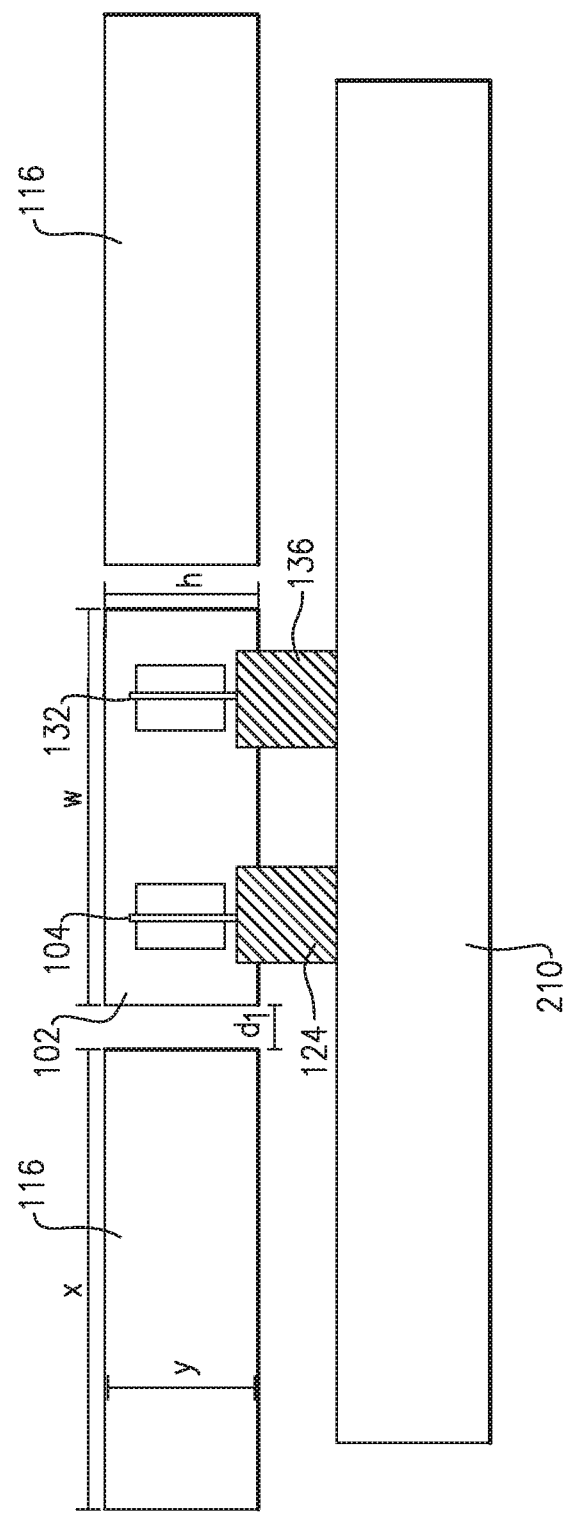
FIG. 2 is a side view of the block diagram of an electric field detector system illustrated in FIG. 1, according to aspects of the present disclosure.

In various examples, the first support 104, second support 106, third support 132, and fourth support 138 act like springs. Movement of the proof-mass 102 is constrained by the spring force of each support, damping forces, and inertial forces. FIG. 1 shows the first support 104, second support 106, third support 132, and fourth support 138, coupled to the proof-mass 102 at an angle substantially perpendicular to the respective surfaces of the proof-mass 102. In certain embodiments, any or all of the first support 104, the second support 102, the third support 132, and the fourth support 138, may be coupled to surfaces of the proof-mass at predetermined angles. Such a configuration may permit detection of axial forces in two linear directions. The ghost-line 144 shown in FIG. 1 demonstrates an illustrative angle α at which the first support 104 may be attached. The second, third, and fourth support 106, 132, 138 may be attached in a similar manner. As the proof-mass 102 may have a plurality of surfaces, in varying embodiments, supports may be attached to any suitable surface of the proof-mass 102. FIG. 2 illustrates an example of a side view of the system 100 according to various embodiments. Views of the second support 106, second sensor, fourth support 138, and fourth sensor are obscured by the first support 104, the first sensor, the third support 132, and the third sensor.

As shown in FIG. 2, the proof-mass 102 may be defined by a length (not shown in FIG. 2), width (w), and height (h). For example, in one implementation the length may be 2000 μm, the width (w) may be 500 μm, and the height (h) may be 500 μm. Similarly, the one or more field concentrators 116 may be positioned at a predetermined distance $d_1$ from the proof-mass 102, and defined by a length (not shown), width (x), and height (y). In one implementation, the one or more concentrators 116 may have dimensions of 50 mm by 2 mm by 0.4 mm, and a gain of 75. In such an arrangement, the concentrators 116 may be arranged at a distance of 200 μm from the proof-mass 102. It is appreciated that variations in the dimensions of the proof-mass 102 may affect the characteristics of the source of concentrated charge. For example, increasing the size of the proof-mass 102 (i.e., also increasing the dimensions of the source of concentrated charge) may result in an increase in the sensitivity of the system 100 to an imparted electric field.

Returning to FIG. 1, the source of concentrated charge generates an electric dipole which produces a torque on the proof-mass 102 when exposed to an electric field. The torque imparted on the proof-mass 102 generates an axial force on the plurality of supports (i.e., first support 104, the second support 106, the third support 132, and the fourth support 138). The torque may be determined directly or indirectly to determine one or more characteristic of the electric field, such as an electric field strength. For example, such axial forces will modify a resonant frequency (e.g., natural frequency) of each support. This may include a first resonant frequency of the first support 104, a second resonant frequency of the second support 106, a third resonant frequency of the third support 132, and a fourth resonant frequency of the fourth support 138. Each support resonates at a particular mechanical resonance when no force is applied. In various embodiments, the controller 112 is coupled to the first electrode 108 and the second electrode 109 of the first sensor, the first electrode 110 and the second electrode 111 of the second sensor, the first electrode 134 and the second electrode 135 of the third sensor, and the first electrode 140 and the second electrode 141 of the fourth sensor. Each sensor is positioned to measure the resonant frequency of the adjacent support and provide a corresponding signal to the controller 112.

For example, the first sensor measures the first resonant frequency of the first support 104, the second sensor measures the second resonant frequency of the second support 106, the third sensor measures the third resonant frequency of the third support 132, and the fourth sensor measures the fourth resonant frequency of the fourth support 138. The controller 112 is coupled to and in communication with each sensor, and configured to execute a series of operations to determine the electric field strength of the electric field imparted on the proof-mass 102 based on the measured resonant frequency of at least one support.

In various embodiments, the plurality of sensors (e.g., the first sensor, second sensor, third sensors, and fourth sensor) may each include a comb drive including a motor component and a sense component positioned on either side of the illustrated comb of a corresponding support. However, in various other embodiments, the sensors may include any other capacitive actuator. For example, the first electrode (e.g., electrodes 108, 110, 134, 140) of each sensor may include the motor component and the second electrode (e.g., electrodes 109, 111, 135, 141) may include the sense component. Alternatively, the second electrode of each sensor may include the motor component and the first electrode may include the sense component.

Each of the motor component and sense component are coupled to and in communication with the controller 112, as shown in FIG. 1. A voltage applied by the motor component causes the motor component, comb, and sense component to be drawn together. The resonant frequency of each support (e.g., first support 104, second support 106, third support 132, and fourth support 138) is proportional to the force developed by the respective sensor. A comb drive capacitance of each sensor may be used to measure the resonant frequency of the support. In particular examples, the controller 112 manages a gain and phase between the motor component and the sense component of each sensor to realize an oscillator which resonates the respective support. In certain other examples, the controller may also manage each sensor to rebalance the system 100 and null changes in the resonator natural frequency.

The axial force exerted on each support as a result of the torque on the proof-mass 102 will cause the support to expand or compress. Stretching will increase the resonant frequency and compression will decrease the resonant frequency. In several embodiments, the controller 112 receives measured signals from the plurality of sensors and the resonant frequency is measured according to:

$$f = f_o\sqrt{1 + \frac{L^2}{\pi^2 EI}B}$$

where, $f_o$, corresponds to the initial resonant frequency of the support at a predetermined value, L, corresponds to the dimensions of the proof-mass, E, corresponds to the applied voltage, I, corresponds to the dimensions of the support, and B, corresponds to the strength of the electric field generated by the source of concentrated charge. In various embodiments, the controller 112 operates in concert with the motor component and sense component of each sensor as an oscillator loop with the resonant frequency as the output.

Various embodiments of the sensors discussed herein may further include a force multiplier positioned to increase the force experienced by each particular sensor. While in one embodiment, changes in resonant frequency may be used to detect the strength of an electric field, in other embodiments, they may be used to detect an acceleration or a change in temperature. As shown in FIG. 1, in one embodiment, the supports may be arranged such that when one support is compressed (e.g., first support 104 is compressed), a second support is expanded (e.g., second support 106 is expanded), or vice versa.

In various embodiments, the controller 112 compares at least one measured resonant frequency, such as the first resonant frequency, to a resonant frequency reference. The frequency reference may include the initial resonant frequency of the particular support, as mentioned above. Based on the comparison, the controller 112 determines the change in resonant frequency to ascertain the torque on the proof-mass 102. The torque on the proof-mass 102 induces the axial force at the end of the respective supports, as also discussed above. Accordingly, the resonant frequency changes as a function of the force during operation of the system 100.

Figure 3:
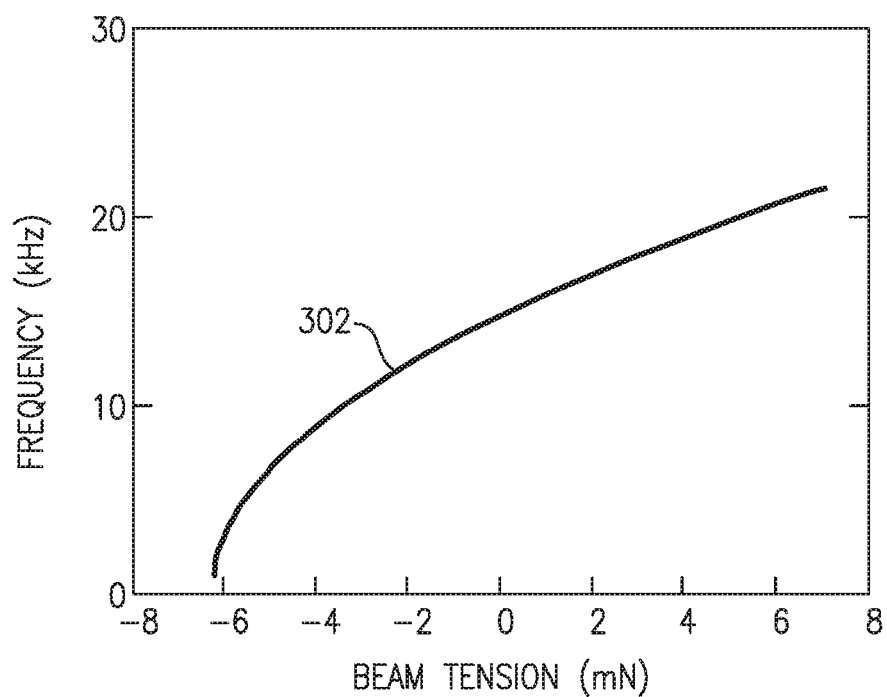
FIG. 3 is a graph demonstrating the relationship between resonant frequency and support tension according to aspects of the present disclosure.

FIG. 3 shows a plot of the relationship between the resonant frequency and the tension in a support, according to various embodiments. As indicated by trace 302, the resonant frequency increases as the tension increases, and decreases as the tension decreases. Accordingly, the torque determined from the resonant frequency, and in particular the change in resonant frequency, may be used by the controller 112 to determine the strength of the electric field. In various embodiments, the resonant frequency includes the natural frequency of the respective support. In one example, the controller 112 may execute a series of instructions to determine the electric field strength according to:

$$\tau = p \times E$$

where, p is the strength (C-m) of the electric dipole generated by the source of concentrated charge, τ is the torque (N-m) on the proof-mass, and E is the electric field strength (V-m).

Similarly, the controller 112 may determine the force of acceleration on the proof-mass 102 based on at least one resonant frequency of the plurality of supports. As described above, with no stress or force on the plurality of supports (i.e., first support 104, second support 106, third support 132, and fourth support 138), the resonant frequency of each support will be a predetermined value (e.g., a resonant frequency reference). However, an axial force imparted on each support will either push or pull the support, thereby increasing or decreasing the resonant frequency of the respective support. The difference between the resonant frequency and the resonant frequency reference represents the force of the acceleration. While in one example, the determined acceleration may include a linear acceleration, in certain other examples the determined acceleration may include a rotational direction.

In further embodiments, a variance in ambient temperature can cause an expansion or compression of the plurality of support members (e.g., support 104, 106, 132, and 138). Such a variance acts like an axial force imparted on the plurality of supports and causes an increase or decrease in the resonant frequency of each respective support. While in some instances, embodiments may include supports that are largely insensitive to temperature changes, in other embodiments, the resonant frequency from one or more supports may be compared to generate a common mode signal. The common mode signal may include a component of an analog signal that is common to the plurality of supports (e.g., the support 104, the second support 106, the third support 132, and the fourth support 138). It is appreciated that ambient temperature changes will have an equal effect on each of the plurality of supports. Therefore, various embodiments of the controller 112 discussed herein may be configured to determine a temperature, and/or one or more temperature changes, based on the common mode signal.

Accordingly, in certain examples, such as the example illustrated in FIGS. 1 and 2, the resonant frequencies of four supports may be measured to determine a torque on the proof mass, a first linear force in a first direction, a second linear force in a second linear direction, and a temperature. It is appreciated that additional supports may be added to determine additional degrees of freedom. In one example, the torque ($\tau$), first linear force ($a_x$), second linear force ($a_y$), and temperature (T), may be determined based on calibration coefficients and the measured resonant frequencies of the plurality of supports ($f_A$, $f_B$, $f_C$, and $f_D$) according to:

$$\begin{bmatrix} ka_\tau & kb_\tau & kc_\tau & kd_\tau \\ ka_{ax} & kb_{ax} & kc_{ax} & kd_{ax} \\ ka_{ay} & kb_{ay} & kc_{ay} & kd_{ay} \\ ka_T & kb_T & kc_T & kd_T \end{bmatrix} \cdot \begin{bmatrix} f_A \\ f_B \\ f_C \\ f_D \end{bmatrix} = \begin{bmatrix} \tau \\ a_x \\ a_y \\ T \end{bmatrix}.$$

Higher order equations and compensation routines may leverage external stimuli such as auxiliary sensors (e.g., gyroscopes, accelerometers, and thermistors) to improve the fidelity of the determinations. The auxiliary sensors may reduce the contribution from error sources and can be used to isolate the received electric field signal from interference effects and error sources.

FIG. 1 shows the proof-mass 102 as having a substantially rectangular profile and having a plurality of planar surfaces. While this may be advantageous for some applications, in other applications the proof-mass 102 may be defined by non-planar surfaces, and may have any suitable shape. According to various embodiments, the proof-mass 102 and the plurality of supports (e.g., supports 104, 106, 132, and 138), are made of silicon material; however, in other embodiments the proof-mass 102 and the plurality of supports may be made of any appropriate material including multiple materials coupled together. Each mechanical ground 124, 126, 136, and 142, may be further coupled, or formed on, a shared substrate, such as a glass (i.e., silicon dioxide) substrate. However, in other embodiments, the mechanical grounds may be attached to any other appropriate material (e.g., silicon). FIG. 2 shows the first mechanical ground 124 and the third mechanical ground 136 coupled to a shared substrate 210. While FIG. 2 illustrates one arrangement of the first mechanical ground 124 and the third mechanical ground 136, in certain other examples, each of the first mechanical ground 124 and the third mechanical ground 136 may have a height which is substantially the same as a distance between the proof-mass 102 and the shared substrate 210 and a height of the respective support (e.g., first support 104 or third support 132), when combined.

In various embodiments, the source of concentrated charge includes a highly resistive dielectric embedded with charge carriers (shown as + and −). According to one embodiment, the source of concentrated charge includes a polarized ferro-electric material including Lithium Niobate. In certain examples, the source of concentrated charge may include an electret; however, in certain other embodiments the source may include other sources of concentrated charge such as one or more capacitor plate having embedded charge carriers. As used herein, the term "electret" refers to the dielectric equivalent of a permanent magnet. For example, an electret configured for use in the system may be formed by: (a) applying heat to the electret material, (b) in response to obtaining a predetermined temperature, applying a voltage to the electret material, at which point the electret material acts like a capacitor and stores the applied charge, and (c) cooling the electret material to a predetermined temperature. Thereafter, the electret maintains a residual charge. As an additional example, the electret material may be bombarded with radiation to generate a residual charge. Accordingly, real surface charges or aligned dipoles are immobilized in the bulk of the dielectric material. Various embodiments of electrets discussed herein may include, but should not be limited to: Thermo-electrets, MPEs (metal-polymer electrets), Radio-electrets, and Mechanoelectrets.

Further embodiments may include a series of two or more stacked electrets or a plurality of electrets arranged in a predetermined order. In order to increase the strength of the electric dipole, and increase the sensitivity of the system to electric fields, micron thick layers of electrets may be stacked. Metal layers may be interposed between the electret layers to increase the gain of one of more field concentrators positioned adjacent the proof-mass 102. For example, the metal layers of some embodiments may include layers of gold or platinum.

Various embodiments discussed herein may include one or more field concentrators located adjacent the proof-mass 102. For example, FIG. 1 shows the field concentrators 116 located proximate a third side 128 and fourth side 130 of the proof-mass 102. Field concentrators 116 may include various flux concentrators, such as electric flux concentrators positioned and arranged to focus the electric field on the proof-mass 102. In some embodiments, field concentrators 116 are formed from a conductive material, such as copper, and are defined by a long and slender profile having a flare at an end. However, in further embodiments field concentrators 116 may include any appropriate structure, material, and shape.

As shown in FIG. 1, the system 100 may include a housing 118. Various components of the system 100 are located within the housing, which protects the components during handling and operation. In one particular embodiment, the housing 118 may include a cryogenic dewar. The cryogenic dewar serves as a cold shield, within which the system components may be cooled, for example, to cryogenic temperatures. Operating the system 100 at cryogenic temperatures reduces Brownian motion and further enhances the signal to noise ratio. In one implementation, the housing 118 is composed of a metal exterior coupled to an electrical ground. It is appreciated that in addition to the numerous benefits discussed herein, embodiments including electrical shielding offer numerous advantageous over traditional magnetic field shielding devices. Generally, magnetic field detector shielding is heavy, cumbersome, and costly. These characteristics make magnetic field detection impractical in many military, covert applications, and medical applications.

While described above as detecting electric field characteristics through the resonance frequency of one or more supports, other embodiments of the system shown in FIG. 1 may include one or more displacement sensors configured to directly measure displacement of the proof-mass. As shown in FIG. 1, one or more sensors 114 may be electrically or optically coupled to the proof-mass 102. For example, an optical sensor may direct optical radiation to and detect reflected radiation from the surface of the proof-mass 102. Movement of the proof-mass 102 may vary reflections of the radiation and enable the optical sensor to track the movement of the proof-mass 102. Although described in one implementation as including an optical sensor, in various embodiments the displacement sensor 114 may include any laser sensor capable of detecting movement of the proof-mass 102.

In other embodiments, movement of the proof-mass 102 may be determined capacitively or using any other method that indirectly determines position and/or forces imparted on the proof-mass 102. For example, the controller 112 may be configured to receive a signal from one or more reference structures, positioned proximate a surface of the proof-mass 102 (e.g., one or more capacitive sensors positioned proximate one or more of the sides 120, 122, 128, 130 and/or a top or bottom surface of the proof-mass 102), indicating a variation in a capacitance between the proof-mass 102 and the one or more reference structures. The controller 112 may then determine the discussed electric field characteristic(s) based on the received signal. While discussed with reference to FIG. 1 as including each of a displacement sensor 114, a capacitive reference structure, and a plurality of sensors positioned to measure a resonant frequency of a corresponding support, in several embodiments the system 100 may include the displacement sensor 114, and/or reference structure, as an alternative to the plurality of sensors.

Accordingly, aspects and embodiments discussed above are generally directed to a system 100 for exploiting the electric component of electromagnetic signals. As discussed, the system 100 may include one or more electric field detectors capable of detecting an electric field generated by the body of a patient, equipment that has been designed to reduce unintended electromagnetic emissions, or equipment that naturally generates very small or attenuated electric and magnetic field signals.

Figure 4:
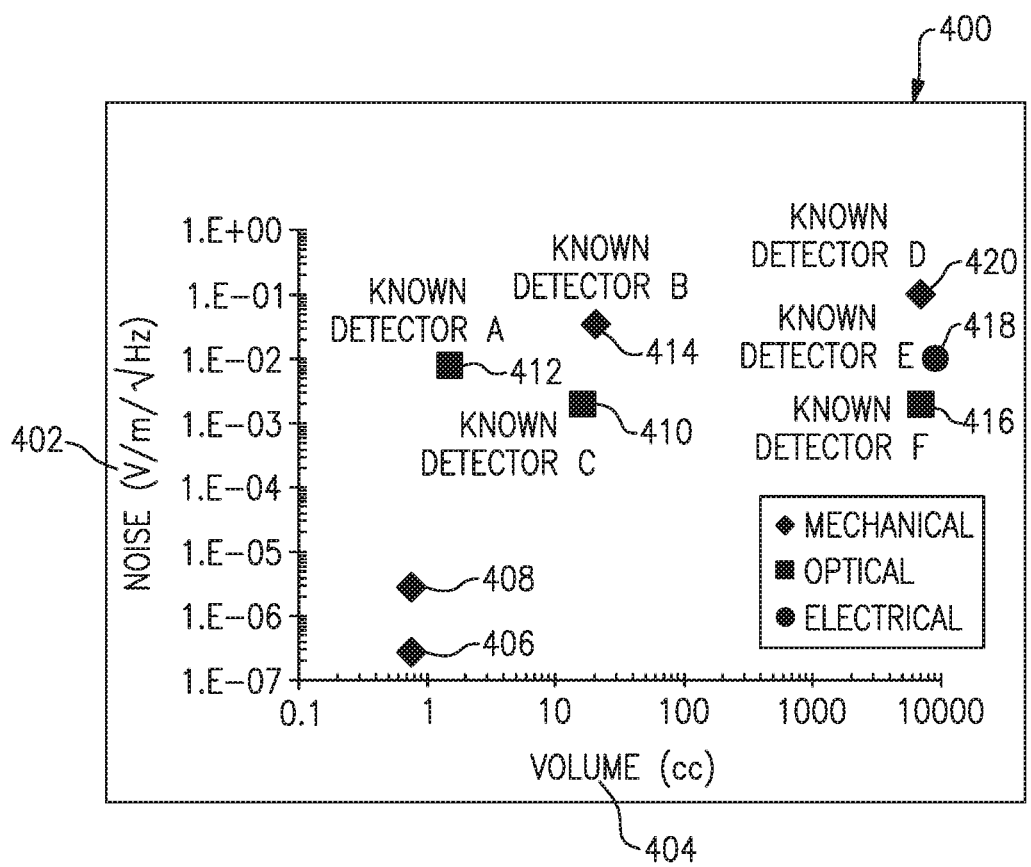
FIG. 4 is a graph demonstrating the improved noise sensitivity of an electric field detector system according to aspects of the present disclosure.

FIG. 4 provides a graph demonstrating the improved noise insensitivity of various embodiments when compared with known electric field detectors. In particular, FIG. 4 demonstrates the noise at 10 Hz. The vertical axis 402 represents the system resolution (V/m/√Hz), and the horizontal axis 404 represents the volume (cc). As discussed above, electric field detectors are typically limited by the total noise that contributes to the measurement of the electric field. The detector itself, and the natural and human environment, all contribute to total noise. Total noise determines the system resolution, in V/m/√Hz. In contrast to conventional detectors, various embodiments provide an ultra-low noise sensor which can observe weak electric field signals of interest. The same result is challenging to achieve with high noise detectors, because the signal of interest is often indistinguishable from noise in the system. As demonstrated in FIG. 4, not only do various embodiments exhibit improved sensitivity (e.g., electric field detector system with a field concentrator data point 406), for equivalent levels of sensitivity, embodiments are volumetrically much smaller (e.g., electric field detector system data point 408) than known detectors. Comparatively, examples of the noise sensitivity of various known detectors are represented by data points 410—420.

Though the components of several views of the drawings herein may be shown and described as discrete elements in a block diagram unless otherwise indicated, the electronic components (e.g., the controller 112) may be implemented as one of, or a combination of, analog circuitry, digital circuitry, or one or more microprocessors executing software instructions, For example, the software instructions may include digital signal processing (DSP) instructions. Unless otherwise indicated, signal lines may be implemented as discrete analog or digital signal lines with appropriate signal processing, or as elements of a wireless communication system. Some of the processing operations may be performed by other analog or digital signal processing techniques and are included within the scope of this application. Unless otherwise indicated, control signals may be encoded in either digital or analog form. Conventional digital-to-analog or analog-to-digital converters may not be shown in the figures.

Figure 5:
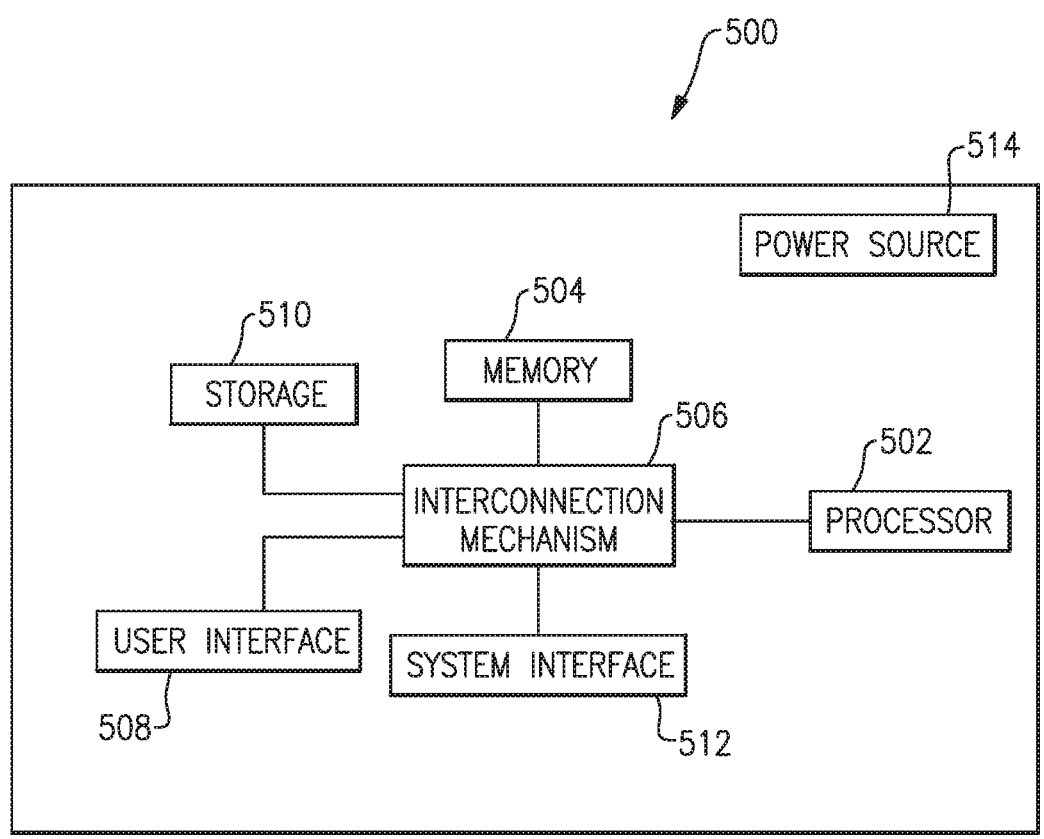
FIG. 5 is a block diagram of one example of a controller according to aspects of the present disclosure.

Referring to FIG. 5, there is illustrated a block diagram of an example of a controller, in which various aspects and functions are practiced. As shown, the controller can include one or more system components that exchange information. More specifically, the controller 500 can include at least one processor 502, a power source 514, a data storage 510, a user interface 508, a system interface 512, a memory 504, and one or more interconnection mechanisms 506. The at least one processor 502 may be any type of processor or multi-processor. The at least one processor 502 is connected to the other system components, including one or more memory devices 504 by the interconnection mechanism 506. In various embodiments, the controller 500 can further include any appropriate signal processing circuitry, such as circuitry configured to execute signal conditioning and electronic control and feedback.

The memory 504 stores programs (e.g., sequences of instructions coded to be executable by the processor 502) and data during operation of the controller 500. Thus, the memory 504 may be a relatively high performance, volatile, random access memory such as a dynamic random access memory ("DRAM") or static memory ("SRAM"). However, the memory 504 may include any device for storing data, such as a disk drive or other nonvolatile storage device. Various examples may organize the memory 504 into particularized and, in some cases, unique structures to perform the functions disclosed herein. These data structures may be sized and organized to store values for particular data and types of data.

Components of the controller 500 are coupled by an interconnection mechanism such as the interconnection mechanism 506. The interconnection mechanism 506 may include any communication coupling between system components such as one or more physical busses in conformance with specialized or standard computing bus technologies. The interconnection mechanism 506 enables communications, including instructions and data, to be exchanged between system components of the controller 500.

The controller 500 can also include one or more user interface devices 508 and system interface devices 512 such as input devices, output devices and combination input/output devices. Interface devices may receive input or provide output. More particularly, output devices may render information for external presentation. Input devices may accept information from external sources. Examples of user interface devices include keyboards, mouse devices, trackballs, microphones, touch screens, printing devices, display screens, speakers, network interface cards, etc. Interface devices allow the controller to exchange information and to communicate with external entities, such as users and other systems via digital or analog input or output streams.

The data storage element 510 includes a computer readable and writeable data storage medium configured to store non-transitory instructions and other data, and can include both nonvolatile storage media, such as optical or magnetic disk, ROM or flash memory, as well as volatile memory, such as RAM. The instructions may include executable programs or other code that can be executed by the at least one processor 502 to perform any of the functions described herein.

Although not illustrated in FIG. 5, the controller 500 may include additional components and/or interfaces, such as a communication network interface (wired and/or wireless), and the at least one processor 502 may include a power saving processor arrangement.

Figure 6:
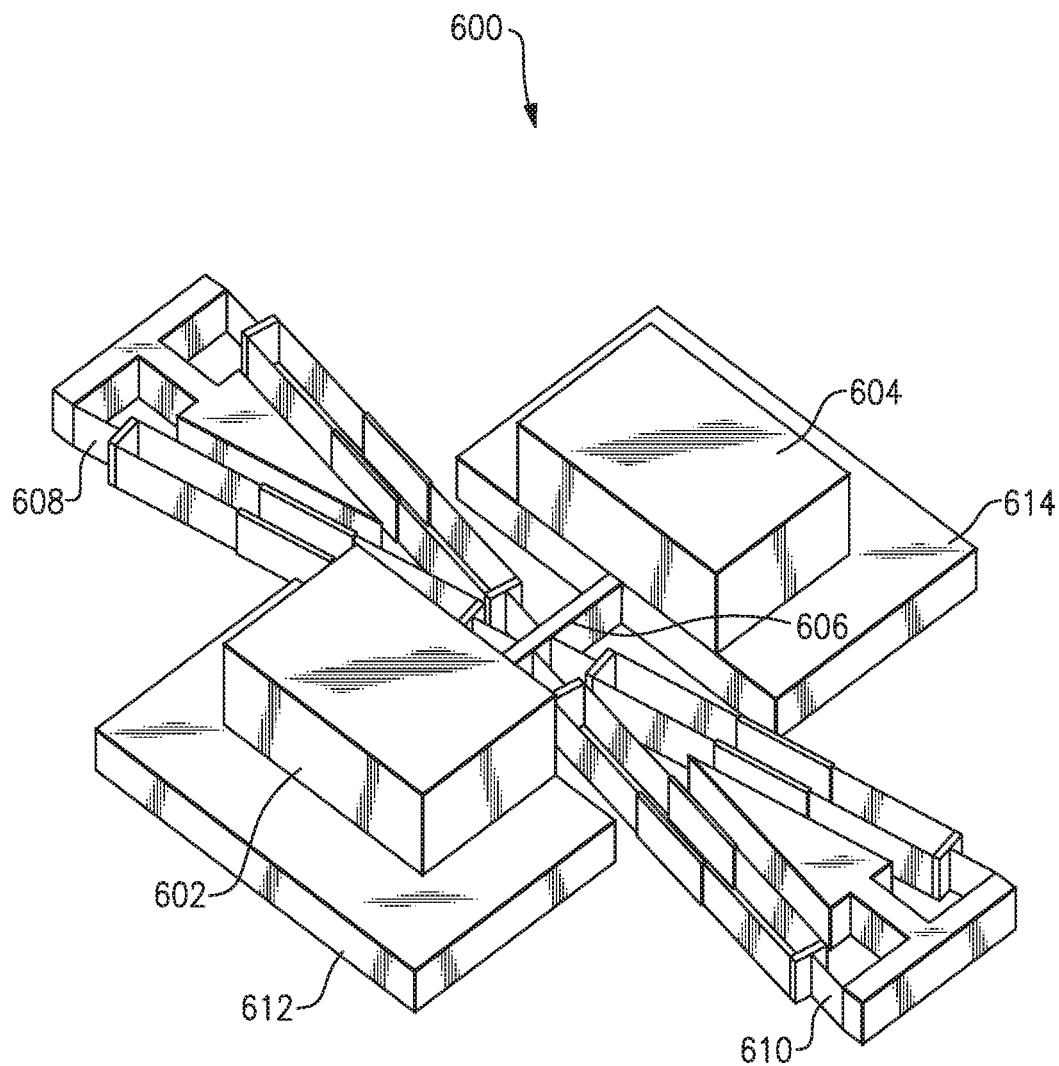
FIG. 6 is a perspective view of an example of an arrangement of an electric field detector according to aspects of the present disclosure.

Referring now to FIG. 6, and with continuing reference to FIG. 1, illustrated is one example of an electric field detector 600 including a separated proof-mass (e.g., proof-mass 102 illustrated in FIG. 1) and source of concentrated charge (e.g., source of concentrated electrical charge). The detector 600 may be included in one or more of the examples of systems described herein, such as the electric field detector system 100 illustrated in FIG. 1. That is, the detector 600 may be coupled with the controller 112, displacement sensor 114, and field concentrators 116, among other components of the system 100 illustrated in FIG. 1.

As discussed with reference to FIG. 1, in certain examples, the source of concentrated charge may include a plurality of sources stacked or separated in a predetermined arrangement. The example of FIG. 6 illustrates a separated proof-mass including a first portion 602 and a second portion 604 divided by an isolation structure 606. Accordingly, in certain examples the source of concentrated charge may include a first portion that is formed on or attached to the first portion 602 of the proof-mass, and a second portion that is formed on or attached to the second portion 604 of the proof-mass. In certain other examples, the proof-mass may be formed from the source of concentrated charge. That is, the proof-mass (e.g., first and second portion 602, 604) may be composed of an electret, for example.

As further discussed below with reference to at least FIGS. 8 and 9A-9B, various embodiments may include one or more isolation restructures, such as a geometric isolation structure and/or an internal isolation structure. Each of the isolation structures may be positioned to isolate the supports 608, 610 from a differential thermal strain between the proof-mass (e.g., first portion 602 and second portion 604) and the supports 608, 610. Such an arrangement may improve the noise performance and/or electric field sensitivity of the electric field detector 600.

In the example of FIG. 6, each support structure 608, 610 is coupled to the internal isolation structure 606, which is arranged as a bridge between the first portion 602 of the proof-mass and the second portion 604 of the proof-mass. Each portion 602, 604 may include a source of concentrated charge arranged in a common direction with the other source of concentrated charge. In particular implementations, the each portion 602, 604 of the proof-mass may be mounted onto a substrate 612, 614. As will be appreciated by those skilled in the art, given the benefit of this disclosure, FIG. 6 shows one example of an arrangement of a separated proof-mass, and other variations in size, shape, and location of the proof-mass can be implemented and are within the scope of this disclosure.

Figure 7:
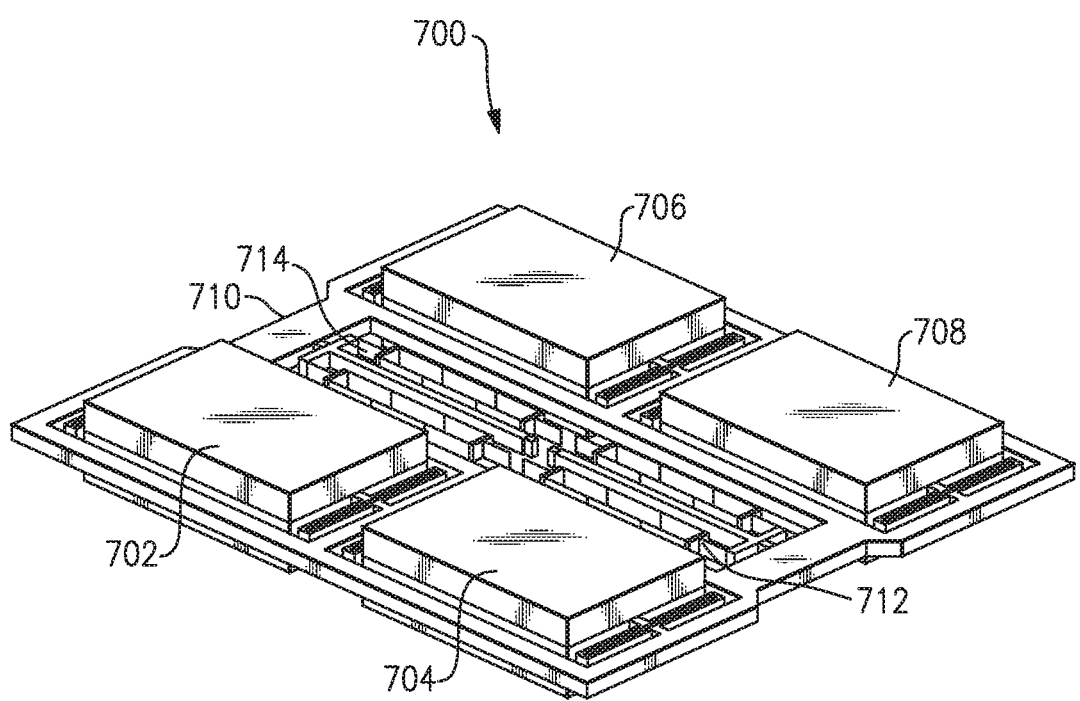
FIG. 7 is another perspective view of an example of an arrangement of an electric field detector according to aspects of the present disclosure.

For example, FIG. 7 illustrates another arrangement of an example of an electric field detector 700 in which the proof-mass is separated into four portions 702, 704, 706, 708. Similar to the detector 600 illustrated in FIG. 1, the detector 700 may be included within one or more of the electric field detector systems described herein. Much like the portions 602, 604 of the proof-mass illustrated in FIG. 6, each of the portions 702, 704, 706, 708 shown in FIG. 7 may include a source of concentrated electric charge in a common direction relative to the other source of concentrated charge. Each portion 702, 704, 706, 708 of the proof-mass may be coupled to a shared substrate 710 which is common to each of the portions 702, 704, 706, 708 of the proof-mass. As further illustrated, in such an arrangement a plurality of supports 712, 714 may be interposed between the portions 702, 704, 706, 708 of the proof-mass, and coupled to the shared substrate 710.

Figure 8:
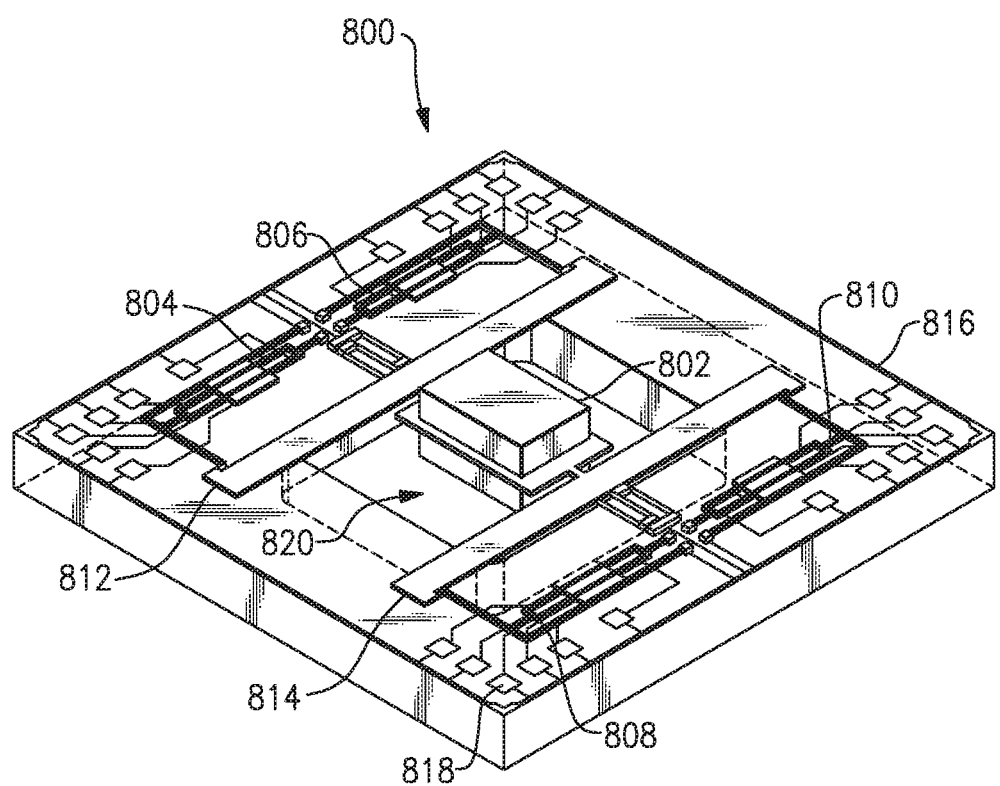
FIG. 8 is a perspective view of one example of an electric field detector system including geometric isolation structures, according to aspects of the present disclosure.
Figure 9A:
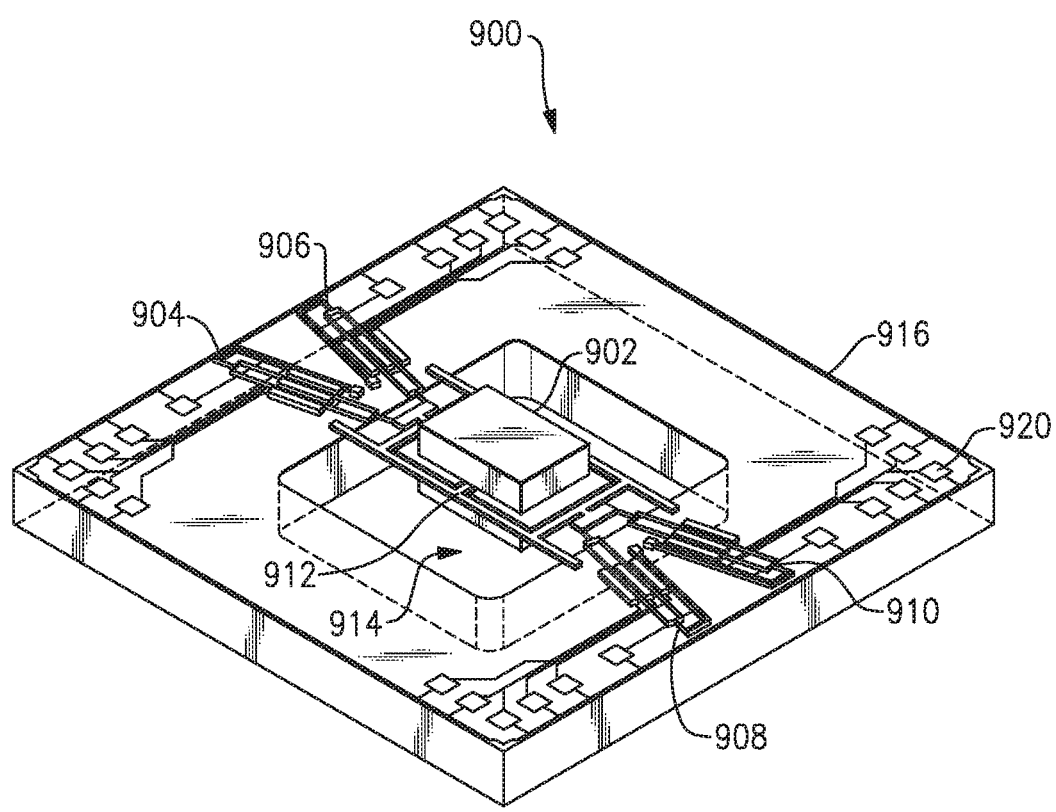
FIG. 9A is a perspective view of one example of an electric field detector system including geometric isolation structures, according to aspects of the present disclosure.

Referring to FIG. 8, there is illustrated an example of an electric field detector system 800 including a plurality of geometric isolation structures 812, 814. As discussed above, in various embodiments the geometric isolation structures 812, 814 may isolate a plurality of supports 804, 806, 808, 810 from a differential thermal strain between a proof-mass 802 and the plurality of supports 804, 806, 808, 810. In particular, FIG. 8 demonstrates an example of an "H-shaped" arrangement which may reduce the sensitivity of the system 800 to errors by substantially isolating the plurality of supports 804, 806, 808, 810 from thermal deformations. In the example of FIG. 8, a first geometric isolation structure 812 is interposed between a first support 804 and the proof-mass 802, and a second support 806 and the proof-mass 802. Similarly, a second geometric isolation structure 814 is interposed between a third support 808 and the proof-mass 802, and a fourth support 810 and the proof-mass 802. Each support 812, 814 may suspend the proof-mass 802 relative to a mounting surface, such as a shared substrate 816 (e.g., silicon substrate). The shared substrate 816 may support additional components of the system 800, and may provide routing for electrical contacts 818. Electrical contacts 818 may be used to electrically couple various components of the system 800, such as a first, second, third, and fourth sensor and a controller.

In the illustrated example, the first geometric isolation structure 812 and the second geometric isolation structure 814 suspend the proof-mass 802 in an opening 820 defined by the shared substrate 816. The opening 820 in the substrate may allow access to a backside of the proof-mass 802, which may make attaching the source of concentrated charge easier. As illustrated, each geometric isolation structure 812, 814 includes a first arm (e.g., fork-shaped arm) coupled to the proof-mass 802 and a second arm (e.g., serpentine-shaped arm) coupled to the respective supports. As shown, each of the geometric isolation structures 812, 814 extend in a direction across the opening that is substantially parallel to a direction of extension of the respective supports. Accordingly, the geometric isolation structures 812, 814 position each support 804, 806, 808, 810 in an orientation that is substantially orthogonal to a direction of thermal expansion of the proof-mass 802. Accordingly, the system 800 includes one or more geometric isolation structures 812, 814 to geometrically reduce the thermal sensitivity of each of the supports 804, 806, 808, 810. In the shown example, each of the support beams 804, 806, 808, 810 is split into a fork to further reduce damping losses.

As also discussed herein, certain embodiments of an electric field detector system may also include one or more internal isolation structures positioned to isolate a plurality of supports (e.g., supports 104, 106, 132, 138 shown in FIG. 1) from a differential thermal strain between a proof-mass (e.g., proof-mass 102 shown in FIG. 1) and the respective supports. Referring to FIGS. 9A-9B, illustrated is an example of an electric field detector system 900 including an internal isolation structure 912. In particular, FIG. 9A shows a perspective view of the electric field detector system 900, and FIG. 9B shows a plan view of the electric field detector system 900. In the example of FIGS. 9A and 9B, the internal isolation structure 912 is interposed between a first support 904, a second support 906, a third support 908, a fourth support 910, and a proof-mass 902. Moreover, FIGS. 9A and 9B demonstrate an example of an "X-shaped" arrangement in which each of the supports 804, 806, 808, 810 has a reduced size to maximize a scale factor and improve the performance of the system 900.

Figure 9B:
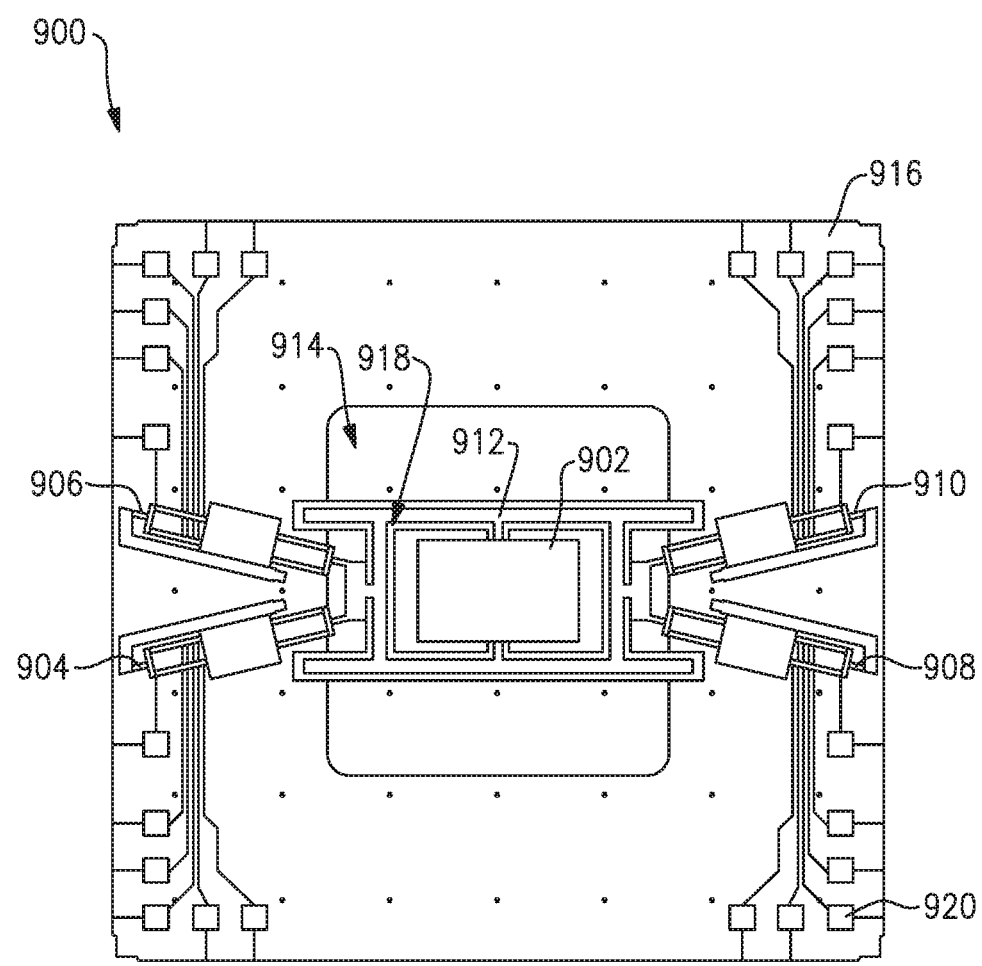
FIG. 9B is a plan view of the electric field detector system illustrated in FIG. 9A, according to aspects of the present disclosure.

As illustrated in FIG. 9B, the internal isolation structure 912 extends through the proof-mass 902 and suspends the proof-mass 902 within an opening 914 defined in a mounting surface, such as a shared substrate 916 (e.g., silicon substrate). In particular, the internal isolation structure 912 may define an aperture along an exterior (e.g., perimeter) of the proof-mass 902 (e.g., illustrated as groove 918). The aperture provides an air gap between the proof-mass 902 and the supports 904, 906, 908, 910, and allows the proof-mass 902 to expand and/or contract without an effect on the respective supports 904, 906, 908, 910. Accordingly, the system 900 includes one or more internal isolation structure 912 which reduce the thermal sensitivity of each of the supports 904, 906, 908, 910. As discussed with reference to the system 800 illustrated in FIG. 8, each of the support beams 804, 806, 808, 810 may be split into a fork to further reduce damping losses. Further, the shared substrate 916 may support additional components of the system 900, and may provide routing for electrical contacts 920. Electrical contacts 920 may be used to electrically couple various components of the system 900 (e.g., the first, second, third, and fourth sensors and the controller 112 shown in FIG. 1).

Referring now to FIG. 10, illustrated is one example of an electric field detector system 1000 packaged within a housing. In certain examples, the housing may facilitate a vacuum environment or cryogenic environment to further reduce damping effects within the system 1000. In the shown example, the housing includes a top cover 1002, an intermediate mounting surface 1004, and a bottom cover 1006. However, in certain other examples the housing may be arranged in other appropriate configurations. In particular implementations, the housing includes one or more attachments which secure the housing to a mobile platform, such as a vehicle. In certain other implementations, the housing may include one or more attachments which secure the housing to a stationary platform.

In various embodiments, the system 1000 may include many of the same components as the system 100 illustrated in FIG. 1 (e.g., the proof-mass 102, the sensors, the plurality of supports, the controller 112, etc.), which are not explicitly described with reference to FIG. 10 for the convenience of description. As illustrated, components of the system 1000 may be mounted on a shared substrate, such as the illustrated printed circuit board 1008. The printed circuit board 1008 may be attached to the bottom cover 1006 of the housing. An internal shield 1010 may extend from the bottom cover 1006 to shield portions of the printed circuit board 1008 and reduce noise interference from electronic components of the system 1000. In certain examples, the internal shield 1010 may be composed of a non-conductive material with a high electric field permeability.

As illustrated, in certain embodiments the system 1000 may include one or more field concentrators 1012 positioned and arranged to focus the electric field on the proof-mass. For example, the field concentrators 1012 may include various flux concentrators, such as any suitable electrically conductive material (e.g., copper). The field concentrators 1012 may be positioned on the intermediate mounting surface 1004 which is configured to rest on a top surface of the internal shielding 1010. When coupled with the internal shielding 1010, an opening 1014 defined in the intermediate mounting surface 1004 rests substantially proximate the proof-mass so as to permit the receipt of electromagnetic radiation at a proof-mass of the system 1000. As further illustrated in FIG. 10, in certain examples the system 1000 may be enclosed by a top cover 1002.

Having described above several aspects of at least one embodiment, it is to be appreciated various alterations, modifications, and improvements will readily occur to those skilled in the art. Such alterations, modifications, and improvements are intended to be part of this disclosure and are intended to be within the scope of the disclosure. Accordingly, the foregoing description and drawings are by way of example only, and the scope of the disclosure should be determined from proper construction of the appended claims, and their equivalents.

What is claimed is:

1. An electric field detector system comprising:
    a proof-mass including a source of concentrated charge configured to generate an electric dipole that produces a torque on the proof-mass in response to an electric field;
    a plurality of supports, each individual support of the plurality supports being coupled to the proof-mass and having a resonant frequency affected by the electric field;
    a plurality of sensors, each individual sensor of the plurality of sensors positioned to measure the resonant frequency of a corresponding support of the plurality of supports; and
    a controller coupled to each individual sensor of the plurality of sensors, the controller configured to measure an electric field strength of the electric field by comparing at least a first measured resonant frequency of the measured resonant frequencies to a first frequency reference to measure the torque on the proof-mass.

2. The electric field detector system of claim 1, wherein the controller is further configured to determine a linear force imparted on the proof-mass, in a first direction, based on at least the first resonant frequency of the measured resonant frequencies.

3. The electric field detector system of claim 1, wherein the controller is further configured to determine a temperature based on a common mode signal generated from a comparison of each of the measured resonant frequencies.

4. The electric field detector system of claim 1, wherein the first frequency reference is a natural frequency of the corresponding support.

5. The electric field detector system of claim 1, wherein the plurality of supports includes a first support coupled to a first side of the proof-mass and having the first resonant frequency, a second support coupled to a second side of the proof-mass and having a second resonant frequency, a third support coupled to the first side of the proof-mass and having a third resonant frequency, and a fourth support coupled to the second side of the proof-mass and having a fourth resonant frequency.

6. The electric field detector system of claim 5, wherein the controller is further configured to determine a first linear force imparted on the proof-mass, in a first direction, and a second linear force imparted on the proof-mass, in a second direction, based on the first resonant frequency, the second resonant frequency, the third resonant frequency, and the fourth resonant frequency, and determine a temperature based on a common mode signal generated from a comparison of each of the first resonant frequency, the second resonant frequency, the third resonant frequency, and the fourth resonant frequency.

7. The electric field detector system of claim 1, wherein the source of concentrated charge includes a polarized ferro-electric material including Lithium Niobate.

8. The electric field detector system of claim 1, wherein the source of concentrated charge includes an electret.

9. The electric field detector system of claim 8, wherein the electret includes a plurality of stacked electrets.

10. The electric field detector system of claim 1, wherein each sensor of the plurality of sensors includes a comb drive including a first electrode configured to apply a voltage to a comb positioned on the corresponding support, and a second electrode configured to measure a change in a capacitance between the first electrode and the second electrode, wherein the controller is further configured to infer the resonant frequency of the corresponding support based at least in part on the change in the capacitance.

11. The electric field detector system of claim 1, further comprising a field concentrator located adjacent a side of the proof-mass, wherein the field concentrator is positioned so as to focus the electric field on the proof-mass.

12. The electric field detector system of claim 1, further comprising a plurality of geometric isolation structures interposed between the proof-mass and each of the plurality of supports, each geometric isolation structure being positioned to isolate a respective support from a differential thermal strain between the proof-mass and the respective support.

13. The electric field detector system of claim 1, further comprising an internal isolation structure extending through the proof-mass and configured to suspend the proof-mass relative to a system substrate, the internal isolation structure being positioned to isolate the plurality of supports from a differential thermal strain between the proof-mass and the plurality of supports.

14. An electric field transduction method comprising:
generating an electric dipole at a proof-mass coupled to a plurality of supports;
receiving an electric field at the proof-mass;
measuring a resonant frequency of each individual support of the plurality of supports; and
determining an electric field strength of the electric field based on at least one measured resonant frequency of the measured resonant frequencies by comparing the at least one resonant frequency to a frequency reference and, based on the comparison, determining a torque imparted on the proof-mass by the electric field.

15. The method according to claim 14, further comprising determining a variability of the electric field based on the at least one measured resonant frequency.

16. The method according to claim 14, further comprising determining a linear force imparted on the proof-mass, in a first direction, based on the at least one measured resonant frequency of the measured resonant frequencies.

17. The method according to claim 14, further comprising determining a temperature based on a common mode signal generated from a comparison of each of the measured resonant frequencies.

18. The method according to claim 14, further comprising determining a force of acceleration imparted on the proof-mass based on the at least one measured resonant frequency of the measured resonant frequencies of the individual supports.

19. The method according to claim 14, wherein the measured resonant frequency of each individual support of the plurality of supports includes a natural frequency.

20. The method according to claim 14, wherein the plurality of supports includes a first support having a first resonant frequency, a second support having a second resonant frequency, a third support having a third resonant frequency, and a fourth support having a fourth resonant frequency, and wherein the method further comprises:
determining a first linear force imparted on the proof-mass, in a first direction, based on the first resonant frequency, the second resonant frequency, the third resonant frequency, and the fourth resonant frequency;
determining a second linear force imparted on the proof-mass, in a second direction, based on the first resonant frequency, the second resonant frequency, the third resonant frequency, and the fourth resonant frequency; and
determining a temperature based on a common mode signal generated from a comparison of each of the first resonant frequency, the second resonant frequency, the third resonant frequency, and the fourth resonant frequency.

* * * * *